United States Patent
Korten et al.

(10) Patent No.: US 9,204,945 B2
(45) Date of Patent: Dec. 8, 2015

(54) SYSTEM COMPRISING A RAPID PROTOTYPING DEVICE AND A MATERIAL CARTRIDGE, A CARTRIDGE, AND A METHOD OF USING THE SYSTEM

(75) Inventors: Malte Korten, Gröbenzell (DE); Helmar Mayr, Kaufering (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 256 days.

(21) Appl. No.: 13/885,018

(22) PCT Filed: Dec. 6, 2011

(86) PCT No.: PCT/US2011/063357
§ 371 (c)(1), (2), (4) Date: May 13, 2013

(87) PCT Pub. No.: WO2012/078533
PCT Pub. Date: Jun. 14, 2012

(65) Prior Publication Data
US 2013/0241095 A1    Sep. 19, 2013

(30) Foreign Application Priority Data
Dec. 9, 2010  (EP) .................................. 10194321

(51) Int. Cl.
B29C 67/00 (2006.01)
A61C 13/20 (2006.01)
A61C 13/00 (2006.01)
A61C 13/09 (2006.01)

(52) U.S. Cl.
CPC ............. *A61C 13/20* (2013.01); *A61C 13/0018* (2013.01); *A61C 13/0019* (2013.01); *A61C 13/0022* (2013.01); *A61C 13/09* (2013.01); *B29C 67/0081* (2013.01); *B29C 67/0085* (2013.01); *B29C 67/0092* (2013.01)

(58) Field of Classification Search
None
See application file for complete search history.

(56) References Cited

U.S. PATENT DOCUMENTS

| | | | |
|---|---|---|---|
| 2,366,516 A | 1/1945 | Geffcken | |
| 2,432,484 A | 12/1947 | Moulton | |
| 2,536,764 A | 1/1951 | Moulton | |

(Continued)

FOREIGN PATENT DOCUMENTS

| | | |
|---|---|---|
| DE | 10235427 | 8/2002 |
| DE | 102007050953 | 10/2007 |

(Continued)

OTHER PUBLICATIONS

Extended European Search Report for EP Application 10 19 4321 dated Jul. 25, 2011, 10 pages.

(Continued)

*Primary Examiner* — Mary F Theisen

(57) ABSTRACT

The present disclosure is directed, inter alia, to a system that comprises a rapid prototyping device and a material cartridge. The rapid prototyping device comprises a chamber for building up the object. The cartridge comprises a body into which a channel extends. A support is adapted to be movably arranged within the channel. The cartridge is adapted to be removably placed in the rapid prototyping device, and the rapid prototyping device can move the support of the cartridge. In one embodiment, the system helps minimizing costs in the manufacturing of dental restorations by rapid prototyping techniques.

11 Claims, 7 Drawing Sheets

(56) References Cited

U.S. PATENT DOCUMENTS

| | | | |
|---|---|---|---|
| 2,601,123 A | 6/1952 | Moulton | |
| 3,337,351 A | 8/1967 | Morehouse | |
| 3,507,897 A | 4/1970 | Kanner | |
| 4,152,165 A | 5/1979 | Langager et al. | |
| 4,338,377 A | 7/1982 | Beck | |
| 4,816,333 A | 3/1989 | Lange | |
| 5,252,264 A | 10/1993 | Forderhase | |
| 5,585,186 A | 12/1996 | Scholz | |
| 5,723,175 A | 3/1998 | Scholz | |
| 5,753,373 A | 5/1998 | Scholz | |
| 6,040,053 A | 3/2000 | Scholz | |
| 6,902,246 B2 | 6/2005 | Varnon | |
| 7,022,416 B2 | 4/2006 | Teranishi | |
| 7,223,364 B1 | 5/2007 | Johnston | |
| 7,476,533 B2 | 1/2009 | Meathrel et al. | |
| 2004/0026418 A1* | 2/2004 | Ederer et al. | 220/23.86 |
| 2004/0084814 A1 | 5/2004 | Boyd | |
| 2005/0275129 A1 | 12/2005 | Sambu | |
| 2007/0126157 A1* | 6/2007 | Bredt | 264/334 |
| 2010/0092765 A1 | 4/2010 | Hager | |
| 2010/0247742 A1 | 9/2010 | Shi | |
| 2012/0119399 A1* | 5/2012 | Fruth | 264/39 |

FOREIGN PATENT DOCUMENTS

| | | |
|---|---|---|
| DE | 102007036370 | 10/2008 |
| DE | 102009020987 | 5/2009 |
| EP | 1764208 | 3/2007 |
| JP | 59-015473 | 1/1984 |
| JP | 60-044147 | 3/1985 |
| JP | 60-044148 | 3/1985 |
| JP | 60-044149 | 3/1985 |
| WO | 02-085246 | 10/2002 |
| WO | 2008-103985 | 8/2008 |
| WO | 2011-141152 | 11/2011 |

OTHER PUBLICATIONS

International Search Report for International Application No. PCT/US2011/063357 mailed on Mar. 22, 2012, 5 pages.

Hattori, Hideshi. 2001. *Adv. Mater.* 13(1):51-54. "Anti-Reflection Surfface with Particle Coating Deposited by Electrostatic Attraction.".

Kang, Hyun Uk et al. 2004. *Korea-Australia Rheology Journal.* 16(4):175-182. "Material and rheological properties of (glycidoxypropyl) trimethoxysilane modified colloidal silica coatings."

Wang et al. 1997. *Nature.* 388:431-432. "Light-induced amphiphilic surfaces.".

Zhai, Lei et al. 2006. *Nano Lett.* 6(6):1213-1217. "Patterned Superhydrophobic Surfaces: Toward a Synthetic Mimic of the Namib Desert Beetle.".

* cited by examiner

SYSTEM COMPRISING A RAPID PROTOTYPING DEVICE AND A MATERIAL CARTRIDGE, A CARTRIDGE, AND A METHOD OF USING THE SYSTEM

CROSS REFERENCE TO RELATED APPLICATIONS

This application is a national stage filing under 35 U.S.C. 371 of International Application No. PCT/US2011/063357, filed Dec. 6, 2011, which claims priority to European Application No. 10194321.5, filed Dec. 9, 2010. The disclosures of both applications are incorporated by reference in their entirety herein.

FIELD OF THE INVENTION

The invention relates to a system which comprises a rapid prototyping device for building up an object, and a material cartridge which can be removably placed in the rapid prototyping device. In particular the invention relates to a cartridge in which the object may be built up and which alternatively may be used to provide at least a component of a build-up material from which the object can be built up.

BACKGROUND ART

In the field of dentistry, the restoration of a patient's tooth or teeth generally includes the replacement of the natural tooth substance by an artificial substance. For larger restorations, pre-finished dental restorations or prostheses are commonly used to replace the tooth or teeth or at least part of those.

Ceramic materials are widely used for making high-quality dental restorations because of their good physical, aesthetic and biological properties. These restorations are often manufactured in automated processes, which typically include at least one or more of the steps of:
digitally capturing the shape of a patient's teeth, for example by scanning a model of the teeth or the actual teeth in the patient's mouth;
making a design of the restoration using computer-aided design (CAD) software;
manufacturing the restoration from the design using a Computer Numerical Controlled (CNC) machine.

There is a general desire to minimize costs for manufacturing of dental restorations. It is further generally desirable to maximize the quality of dental restorations.

SUMMARY OF THE INVENTION

In one aspect the invention generally relates to a system which comprises a rapid prototyping device which is adapted to make a dental restoration or a precursor of a dental restoration from a build-up material. In particular the system of the invention comprises a rapid prototyping device and a material cartridge. The rapid prototyping device is suitable for building up a three-dimensional object from a build-up material. A build-up process as provided by the rapid prototyping device of the invention may also be referred to as "additive manufacturing process". Such a build-up process may for example provide an object by successively adding smaller amounts of build-up material to one another to form the object. This is in contrast to a subtractive process in which an object is typically machined out of a larger blank of material, for example by grinding or cutting. The build-up material may in particular be or comprise a ceramic or glass-ceramic material. In other embodiments the build-up material may further be a liquid or pasty composite, for example a hardenable composite.

The rapid prototyping device of this system comprises at least a first chamber for building up the object from the build-up material.

Further the cartridge of the system comprises:
a body into which a channel extends;
the channel forming a first cartridge opening in the body;
a support which is adapted to be movably arranged within the channel for a movement relative to the first cartridge opening;
the cartridge being adapted to be removably placed in the first chamber; and
the cartridge being adapted to form a reservoir, preferably for the object and/or the build-up material;
wherein the rapid prototyping device and the cartridge are adapted such that the rapid prototyping device can move the support of the cartridge, and wherein the rapid prototyping machine is adapted such that the presence of a cartridge is optional for building up the object. Thus the object preferably can be built up in the reservoir of a cartridge present in the first chamber and/or in the first chamber outside the reservoir in absence of the (or any) cartridge.

The invention may be advantageous in that it may allow the use of a standard rapid prototyping device for making a dental product. In particular rapid prototyping devices which are typically configured for building up larger objects may be enabled for building up comparatively small dental restorations. Further the invention may help minimizing a contamination of the built-up dental restoration and/or the material used for building up the dental restoration. The invention may further allow for building up two or more objects from different build-up materials in parallel or simultaneously. For example different build-up materials may be used for simultaneously creating differently colored objects. The invention may further help minimizing waste of build-up material, in particular in case a small object is built up in a standard rapid prototyping device. The invention may also allow for providing a certain predetermined amount of build-up material depending on the size of the object to be built up, for example by providing differently sized cartridges. Further the cartridge of the invention preferably allows for quickly and conveniently removing of an object built up in a rapid prototyping device together with removing the cartridge. The cartridge of the invention further preferably allows separating the built up object from surrounding build-up material by way of screening. The invention may further be advantageous in that it may help maximizing the throughput of a rapid prototyping device. Overall the invention may thus help minimizing costs for manufacturing dental restorations and maximizing the quality of finished dental restorations.

In one embodiment the first chamber of the rapid prototyping device comprises a first base which is movable in the first chamber relative to a first chamber opening. Such a movement is preferably provided in a Z-dimension of a three-dimensional Cartesian X, Y, Z coordinate system as further referred to in this specification. The skilled person will recognize that a movement of the first base relative to the first chamber opening may be replaced by a movement of the first chamber opening relative to the first base or by a movement of both the first base and the first chamber opening relative to each other as equivalent solutions. The first base may further be adapted to carry at least a first component of the build-up material. Further the first base may be movable toward and away from the first chamber opening. In more particular the first base may be movable stepwise away from the first chamber opening for receiving the first component in layers that have similar or generally equal thicknesses. The first base may initially be positioned generally flush with the first chamber opening. For example the base may not extend outside the chamber beyond the first chamber opening. From the initial position the first base may be moved away from the first chamber opening into the chamber by a predefined distance such that a predefined space is formed between the first chamber opening and the first base. That space may be filled with the first component to form a first layer of the first component on the base. The layer of the first component thus has a thickness in the Z-dimension. For depositing a second layer of the first component to the first layer the base is preferably positioned farther away from the first chamber opening by the same predefined distance such that the same predefined space is formed between the first chamber opening and the first layer. That space may again be filled with an amount of the first component so that a second layer of a thickness generally equal to the thickness of the first layer may be provided on the first layer. Further layers may be provided by sequentially moving the base and depositing further amounts of the first component.

In each layer one or more generally solid particles may be generated in different ways as described in the examples of this specification. The particles may be generated at predetermined positions in the X and Y dimension of the layer and may extend in the Z-dimension through the entire layer. Several adjoining particles may form the object built up by the rapid prototyping device.

In one embodiment the rapid prototyping device of the system comprises a dispensing unit for providing a second component. The second component may be provided to a layer of the first component already deposited in the first chamber. The dispensing unit may therefore be movable at least in the X- and Y-dimension. In particular the dispensing unit may be movable in the X- and Y-dimension within part or the entire area of the first chamber opening. Again the skilled person will recognize that likewise the first chamber opening may be moved relative to the dispensing unit or that both the first chamber and the dispensing unit may move relative to each other. Therefore the rapid prototyping device may be adapted to build up an object from a powder material as a first component and a liquid as a second component, for example. The rapid prototyping device may further have a heating, illumination or laser illumination unit which is movable in the X- and Y-dimension within part or the entire area of the first chamber opening. The skilled person will again regard any movement causing a relative movement between the unit and the first chamber as equivalent solutions. Thus the rapid prototyping may be further adapted to build up an object from a heat or light hardenable material provided as a first component.

In a further embodiment the rapid prototyping device further comprises a second chamber for providing or storing at least a component of the build-up material. In this embodiment the cartridge is preferably further adapted to be removably placed in the second chamber, and wherein the rapid prototyping machine is preferably further adapted such that the presence of a cartridge is optional for providing the build-up material. Thus the build-up material preferably can be provided in the reservoir of a cartridge present in the first chamber and/or in the second chamber outside the reservoir in absence of the (or any) cartridge.

The second chamber of the rapid prototyping device may comprise a second base which is movable in the second chamber relative to a second chamber opening. Such movement is preferably also provided in the Z-dimension. The skilled person will recognize that a movement of the second base relative to the second chamber opening may be replaced by a movement of the first chamber opening relative to the second base or by a movement of both the second base and the first chamber opening relative to each other as equivalent solutions. The second base may be adapted to carry at least a first component of the build-up material. Further the second base may be movable toward and away from the second chamber opening. In more particular the second base may be movable stepwise toward the first chamber opening for displacing the first component out of the second chamber opening. The second base may initially be positioned away from the second chamber opening. The space between the second chamber opening and the second base may be filled with the first component. From the initial position the second base may be moved toward the second chamber opening by a predefined distance such that a predefined amount of the first component protrudes out of the second chamber over the second chamber opening.

In a further embodiment the rapid prototyping device comprises a recoater which is adapted to displace the amount of the first component protruding over the second chamber opening toward the first chamber opening. Thus individual amounts of the first component may be transferred from the first chamber toward the second chamber to generate individual layers from the amounts from the first chamber.

In one embodiment the system further comprises a plunger which is adapted to cooperate with the cartridge for moving the support. The system may be further adapted such that the plunger cooperates with the first or the second base of the rapid prototype device, and in particular such that a movement of either the first or the second base of the rapid prototype causes the same movement of the plunger. The plunger may be fixed (for example magnetically adhered, adhesive bonded, screwed) to the first or second base, but may in other embodiments just stand on the first or second base. Further the plunger may form a removable part of the cartridge.

In a further embodiment the channel extends with a generally uniform cross-section within the body along a longitudinal axis of the cartridge. The cartridge may be placed in the rapid prototyping device with the longitudinal axis oriented generally parallel to the Z-dimension. Further the channel may extend between the first cartridge opening and an opposite second cartridge opening in the body. The channel may further be adapted such that the plunger can be at least partially arranged within the channel between the support and the second cartridge opening. This preferably allows for the plunger and the support to cooperate, for example to abut or engage with one another, for moving the support. The plunger and the support may further be adhered to each other magnetically.

In a further embodiment the system is adapted such that the plunger can position the support between a first position in which the support is spaced relative to the first cartridge opening and a second position in which the support is substantially flush with the first cartridge opening. The support may be freely positioned in any intermediate position between the first and second positions within the channel.

In one embodiment the plunger and the body are adapted to self-align relative to one another in at least the second position. The self-alignment preferably provides the plunger and the body to align relative to each other toward a predefined position on a plane that is generally perpendicular to the longitudinal axis. This may allow a loose fit between the plunger and the body in other positions than the second position, but nevertheless allows for aligning the plunger and the body in at least the second position relative to each other. Thus a generally friction free but nevertheless precise cooperation of the plunger and the body with one another may be achieved.

In a further embodiment the plunger and the channel are sized such that in a plane generally perpendicular to the longitudinal axis a circumferential gap is formed between walls forming the channel and the plunger. The gap is preferably sized to permit the first component to flow through. Thus a generally friction free cooperation of the plunger with the body may be achieved with a component of the build-up material present in the cartridge.

In one embodiment the support comprises a plurality of through-holes. The system may be further adapted such that the plunger blocks the through-holes, preferably all of the through holes, during cooperation with the support for moving the support. Further the system may be adapted such that the piston opens the through-holes in a situation where the plunger is removed from the support. This preferably allows the cartridge to hold the first component of the build-up material during use for providing material into the rapid prototyping device or for building up an object. Further this preferably permits at least the first component to be released from the cartridge via the through-holes. Thus an unused amount of the first component may be removed from an object built up in the cartridge with the object being retained within the cartridge. Further it has been found that a powder material can be distributed on the support which comprises through-holes more uniformly relative to a support without through-holes. The through-holes may for example provide for a retention of the powder material which hinders the powder in sliding on the surface of the support.

In a further embodiment the body comprises a spillover cavity adjacent the first cartridge opening. The spillover cavity may allow for gathering material which is unintentionally positioned to the cartridge outside the cartridge opening. Thus the rapid prototyping device may be kept relatively clean from such material during use.

In one embodiment the cartridge has a first side face having a first structure and a second side face having a second structure. The first and second structures preferably have complementary shapes, for example one face may have the negative structure of the other face. The first and second faces preferably face away from each other, for example are arranged at opposite sides of the cartridge. This preferably allows for placing two similar cartridges with their complementary faces in contact side by side such that the two cartridges are arranged in a predetermined position with one another. Preferably in such a predetermined position of the cartridges relative to each other the cartridge openings are generally in a common plane.

In one embodiment the system comprises a retention mechanism for retaining the cartridge in the rapid prototyping device. In particular the system may comprise a retention mechanism for retaining the cartridge in the first of the second chamber of the rapid prototyping device. The retention mechanism may for example comprise at least one of a clamping device, a magnet, and a mechanical lock. The clamping device may provide for urging the cartridge to a wall of the first or second chamber. The magnet may be provided in the cartridge and/or the chamber wall to urge the cartridge to the wall. Further a mechanical lock may comprise a positive fitting between the cartridge and the chamber wall, like a hook and loop, screw or any other suitable connection.

In a further embodiment the system comprises a cartridge of the invention in the first chamber and a further cartridge of the invention in the second chamber.

The system is preferably adapted to be selectively operated for building up an object with a cartridge placed in the first and/or second chamber(s), or with any cartridges removed from the first and/or second chamber(s). For example no cartridge may be present in the first and/or second chamber(s). Further the first and second chambers are preferably configured such that within the first chamber an object can be directly build up and such that within the second chamber powder can be directly stored. For example the first and second chambers preferably provide a sufficient seal to prevent powder from escaping through a gap between the movable base and the walls of the respective first and/or second chamber(s). Such a seal may not be present in the cartridge (for example may not be present between the support and the channel walls) although the cartridge preferably sufficiently is adapted to avoid major leaking of the powder material from the cartridge. Thus the support may be movable within the channel at minimized friction. Further powder material unintentionally moving between the support and the channel walls may remove automatically. Further due to the cartridge being placeable or placed in sealed chambers of the rapid prototyping device powder material unintentionally escaping from the cartridge may be hindered from flowing toward sensitive components inside of the rapid prototyping device.

The system is preferably adapted to be operated in a first operation mode in which a cartridge is placed in the first chamber, wherein in this first operation mode the object is built up within the cartridge, and in a second operation mode in which the cartridge is removed from the first chamber (for example in which no cartridge is present in the first chamber), wherein in this second operation mode the object is built up within the first chamber. Further the system is preferably adapted to be operated in a third operation mode in which a cartridge is placed in the second chamber, wherein in this third operation mode a powder material for building up the object can be supplied from the cartridge, and in a fourth operation mode in which the cartridge is removed from the second chamber (for example in which no cartridge is present in the second chamber), wherein in this fourth operation mode a powder material for building up the object can be supplied from the first chamber. Further operation modes may be formed by combinations of the first, second third and fourth operations modes, for example:

a combination of the first and third operation mode;
a combination of the first and fourth operation mode;
a combination of the second and third operation mode; and
a combination of the second and fourth operation mode.

In one embodiment the first component of the build-up material is a powder, in particular a glass powder. In this embodiment the second component is preferably a liquid, in particular a water based liquid.

In a further embodiment the cartridge may have an identification code. The cartridge may for example have an RFID tag which stores the identification code. The rapid prototyping device may have an RFID reader which is adapted to read the identification code from the RFID tag. The rapid prototyping device may select operation parameters, and in particular select data about the shape of the object, according to the identification code. The identification code may for example be assigned to a certain patient who shall receive a dental restoration obtained from the object built up. Therefore the system of the invention may be advantageous because it preferably allows for automation.

In one embodiment the body is made by a build-up process from a build-up material. Further the support may be made by a build-up process from a build-up material. And further the plunger may be made by a build-up process from a build-up material.

In a further aspect the invention relates to a material cartridge. The material cartridge is adapted for being removably placed in a rapid prototyping device for building up a three-dimensional object, the cartridge comprising:
a body into which a channel extends;
the channel forming a first cartridge opening in the body;
a support for holding at least a component of the build-up material;
the support being adapted to be movably arranged within the channel for a movement relative to the first cartridge opening; and
wherein the support comprises a plurality of through-holes.

The configuration of the material cartridge may further correspond in configuration to the various embodiments of the cartridge described for the system of the invention.

In another aspect the invention relates a method of making at least a part of a dental restoration. The method comprises the steps of:
providing a rapid prototyping device for building up a three-dimensional object;
providing a first cartridge in the rapid prototyping device;
building up the object in the cartridge;
removing the first cartridge from the second chamber.

The method preferably provides for minimizing the time for removing the built up object from the rapid prototyping device. This is because the cartridge may allow for example to remove the object together with excess material needed to build up the object so that a separation of the object from such material may be performed outside the device while the device is used to build up a new object. Further the method may comprise the step of shaking at least part of the first cartridge on a vibrating unit. Thus the excess material may be quickly and efficiently removed from the object by sieving the object from the material within the cartridge of the invention.

In one embodiment the method further comprises the step of providing at least a component of the build-up material within a second cartridge into the rapid prototyping device.

DETAILED DESCRIPTION OF THE INVENTION

Figure 1:
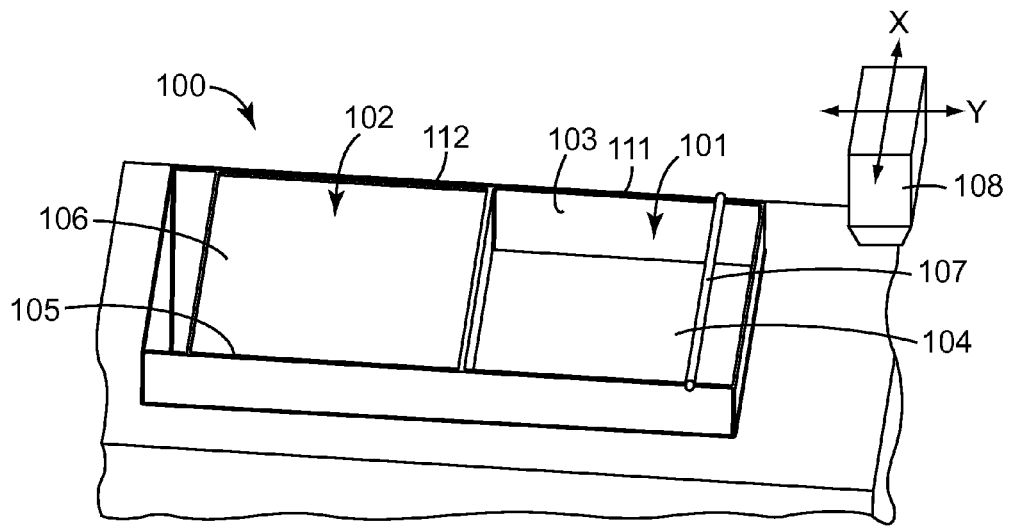
FIG. 1 is a partial perspective view of a rapid prototyping device as it may be used with the present invention.

FIG. 1 is a partial perspective view of a rapid prototyping device 100 as it may be used with the present invention. The device 100 is generally adapted to build up a three-dimensional object based on digital data which represent a shape of that object. Therefore the device 100 may be generally referred to as "3D printer". In particular the device 100 is preferably adapted to build up a mechanically stable three-dimensional object from a build-up material. The build-up material is further described with reference to a powder material and a liquid used for solidifying portions of the powder material by way of example only. Such a powder material may in the example be provided in the form of generally free flowing or loose grains. Other rapid prototyping devices may only use a single component like a liquid, a paste or a powder. Such a single component may be locally hardened for example by light and/or heat. There are other rapid prototyping devices using two or more components selected from any of a liquid, a paste, or a powder which may likewise be usable with the present invention.

The device 100 of the example has a first chamber 102 formed by first side walls 105 and a first base 106 surrounded by the first side walls 105. Further the device 100 has a second chamber 101 for containing powder material (the figure shows the second chamber at an empty stage without any powder). The second chamber 101 thus may serve as a supply for the powder material used in the device 100 for building up the object. The second chamber 101 is formed by second side walls 103 and a movable second base 104 surrounded by the side walls 103. The first and second chambers 102, 101, form first and second chamber openings 112, 111 respectively. In particular the first and second chambers 102, 101 are open in an upward direction. An "upward direction" within the meaning of this specification generally refers to a direction opposite to a direction of the force of gravity.

Thus for example a powder contained in any of the first or second chambers 102, 101 may normally stay within the chamber by gravity. The first and second bases 106, 104 are preferably arranged such that they can displace (for example lift or lower) a material contained in the first and second chambers 102, 101, respectively, relative to the corresponding first and second chamber openings 112, 111. In the example the first and second bases 106, 104 are movable toward and/or away from the chamber openings 112, 111. The device 100 further has a recoater 107 which is adapted for transferring powder from the second chamber 101 toward the first chamber 102. Further the device has a dispensing unit 108 for selectively providing a liquid to portions of the powder. The dispensing unit 108 is movable in at least two dimensions (as indicated by the arrows X, Y) and may be positioned at defined positions over at least the first chamber 102.

Figure 2:
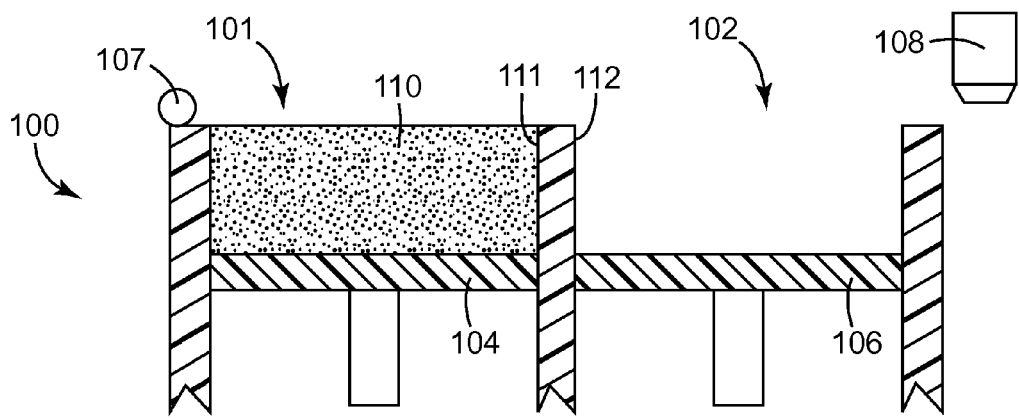
FIGS. 2-6 are schematic views illustrating the operation of the rapid prototyping device shown in FIG. 1.
Figure 6:
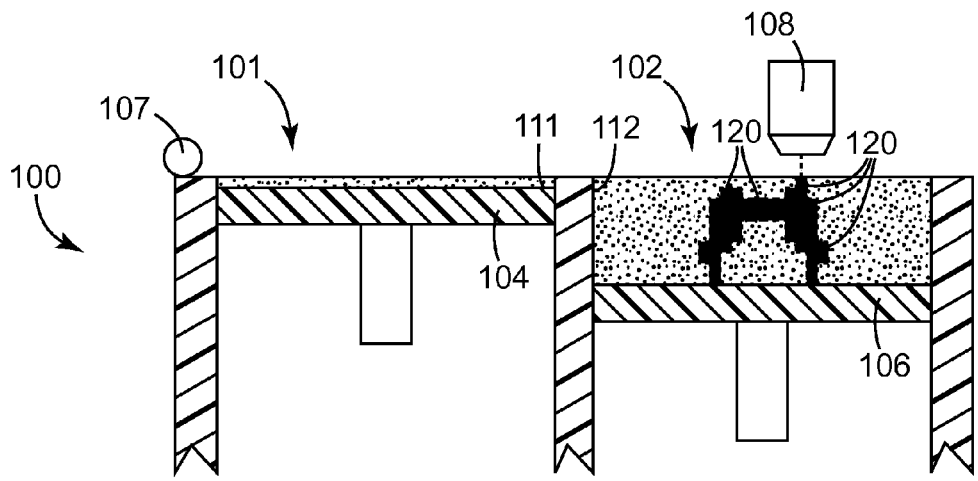

FIG. 2 throughout FIG. 6 illustrate the operation of a rapid prototyping device of the type shown in FIG. 1.

FIG. 2 shows the rapid prototyping device 100 at an initial stage. In the initial stage the first chamber 102 is empty or substantially empty, whereas the second chamber 101 contains a powder material 110. The second base 104 is positioned at an initial lower level such that the powder level is substantially flush with the second opening 111 of the second chamber 101. The first base 106 may be positioned at an initial lower level as shown or may be positioned further toward or flush with the first chamber opening 112.

Figure 3:
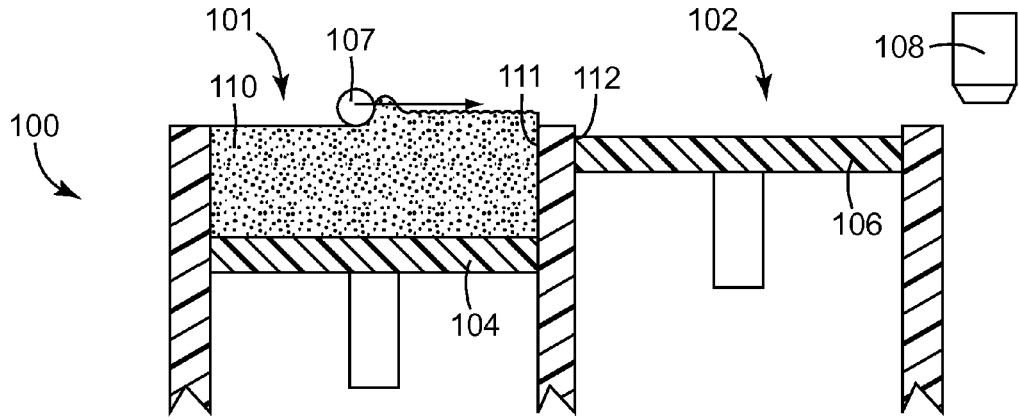
Figure 4:
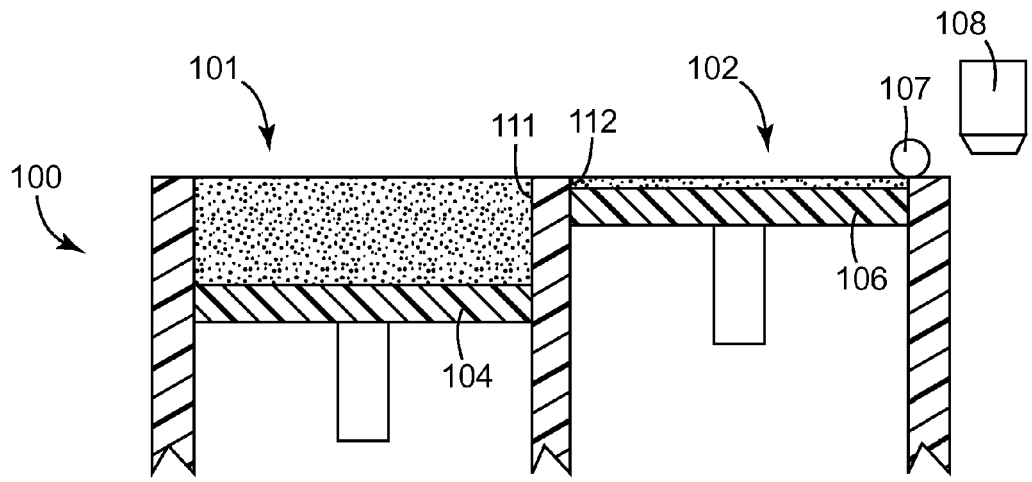

FIG. 3 shows the second base 104 lifted by a predetermined distance relative to the initial level shown in FIG. 2. Thus a predetermined quantity of the powder material is lifted such that it protrudes above the second chamber opening 111 of the second chamber 101. The first base 106 is positioned by approximately the same predetermined distance below the first chamber opening 112. The recoater 107 is indicated in a position within a travel of the recoater from the second chamber 101 toward the first chamber 102 (in the Figure from the left toward the right) for transferring the powder protruding from the second chamber opening 111 toward the first chamber 102. The recoater 107 preferably wipes over the entire second chamber opening 111 of the second chamber 101. Therefore substantially all of the powder protruding over the second chamber opening 111 may be pushed by the recoater and transferred toward the first chamber 102 as shown in FIG. 4. In the example shown in FIG. 3 and FIG. 4 the first base 106 is positioned such that the capacity of the first chamber 102 substantially corresponds to the powder quantity protruding over the second chamber opening 111. Therefore the powder quantity protruding over the second chamber opening 111 preferably substantially exactly fits within the first chamber 102. The recoater 107 preferably wipes over the entire first chamber opening 112 of the first chamber 102 and therefore preferably levels the powder to flush with the first chamber opening 112 of the first chamber 102, as it is illustrated in FIG. 4. In this way a layer of powder having a defined thickness is provided in the first chamber 102.

Figure 5:
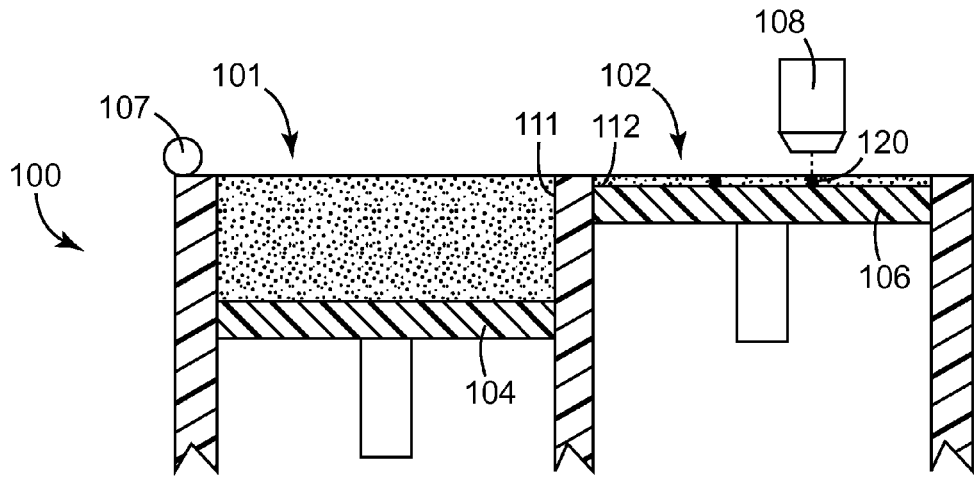

FIG. 5 shows the powder layer in the first chamber 102. The recoater is positioned outside areas above the first and the second chamber openings 112, 111 of the first and second chambers 102, 101, respectively. The dispensing unit 108 is positioned over the first chamber opening 112 of the first chamber 102. Further a liquid 120 is provided on the powder layer. In particular a predetermined dose of the liquid (for example a droplet) is provided on the powder at a predetermined coordinate in a plane of the first chamber opening 112 of the first chamber 102. Therefore a portion of the powder adjacent that coordinate may be penetrated by the liquid. The powder and the liquid getting into contact with one another preferably causes forming of a generally solid particle. Such a particle is preferably greater than the individual grains of the powder.

The liquid may be a hardenable binder or may be adapted to cause the powder grains to connect with one another, for example to adhere to each other or to fuse with one another. In one embodiment the liquid comprises mostly water and a small amount of organic additives, and the corresponding powder comprises polymer covered glass powder. In another embodiment the liquid is a hardenable binder. Therefore the liquid may be generally adapted for penetrating the powder and to cause the powder in combination with the liquid to form a generally solid particle of a predetermined size. In case the water based liquid is used the water may be substantially entirely removed after the grains are connected with each other. Further in case the liquid is a hardenable binder the hardened binder may form a generally solid matrix for the powder grains.

The properties of the powder and the liquid may be adapted to control the size and shape of the generated particles. For example the liquid and the powder may be adapted such that the liquid typically penetrates the powder relatively deeply whereas it may typically not widely spread laterally in the powder material. Thus the penetration depth may be greater than the penetration width so that the formed particle may be relatively tall and narrow. The liquid and the powder may further be adapted such that the liquid typically relatively quickly spreads in the powder laterally but penetrates less deeply in the powder. Thus the formed particle may therefore be generally flat. Further the amount of liquid may be used to control the overall volume of the particle. Relevant properties may comprise viscosity, wettability, and chemical interaction between the liquid and the powder, for example.

In the example the amount of liquid and the properties of the liquid and powder are adapted such that the thickness of the powder layer in the first chamber 102 can be substantially penetrated entirely by the liquid. Therefore the height of a particle formed in the layer may typically exactly correspond to the thickness of the layer. The penetration width may substantially correspond to the layer thickness, or may be smaller. For example the thickness of the powder layer may be about 80 µm and the width may be about 50 µm.

A larger three-dimensional object may be created by providing further powder layers into the first chamber 102 in which further particles are generated. Liquid penetrating through an upper powder layer may contact a particle of a lower layer and thus may result in upper and lower particles to connect with each other. Further laterally adjacent particles may be formed in contact to each other and therefore connect to one another. A larger object therefore may be created by providing powder layer by layer and by providing liquid in a two-dimensional pattern on each of several consecutive layers as indicated in FIG. 6.

FIG. 6 shows the device 100 with several powder layers in the first chamber 102. The first base 106 is lowered relative the stage shown in FIG. 5 so that the top most powder layer is substantially flush with the first chamber opening 112 of the first chamber 102. A plurality of particles 120 are provided in the powder, for example by way of powder layering and liquid dispensation as described. In the example at least part of the particles 120 are connected to one another and form a precursor of a dental restoration. Such a dental restoration precursor may be removed from the surrounding generally loose powder and used in the preparation of a dental restoration.

A dental restoration precursor as it may be obtained from processing a powder material may have a generally porous material structure. This means that powder grains may be in contact with one another but form spaces between. Such a dental restoration precursor may in a subsequent step by sintered (for example exposed to heat) to transform the porous material structure in a generally non-porous material structure. Thereby the dental restoration precursor may proportionally shrink in it three dimensions. Accordingly the dental restoration precursor may be proportionally oversized relative to the final dental restoration. The dental restoration precursor may further be pre-sintered only, so that the material structure is still porous but the material stability is increased relative to the non-sintered stage.

Figure 7:
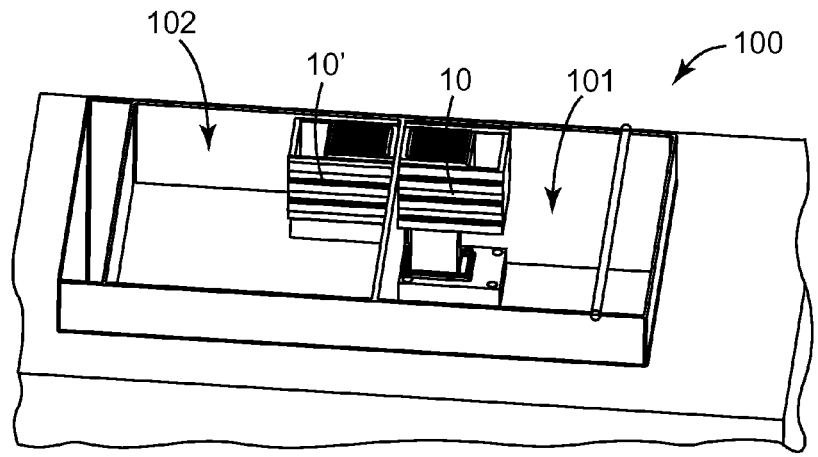
FIG. 7 is a perspective view of the device shown in FIG. 1 with two material cartridges according to an embodiment of the invention.

FIG. 7 shows the device 100 with material cartridges 10, 10' according to the invention. The material cartridges 10, 10' are placed within the second chamber 101 and the first chamber 102, respectively. In this example a powder material may be provided within the material cartridge 10 and the object may be built up within the preferably identically configured material cartridge 10'. This means that the powder material may not be provided directly within the second chamber 101, and the object may not be directly built up in the first chamber 102. In contrast the powder material is preferably indirectly provided within the second chamber 101, and the object is preferably indirectly built up in the first chamber 102. However the process of building up the object may generally correspond to the process described in FIGS. 1-6 except that the powder is provided in a cartridge, and the object is built in a further cartridge instead of directly in the chambers of the device.

Figure 8:
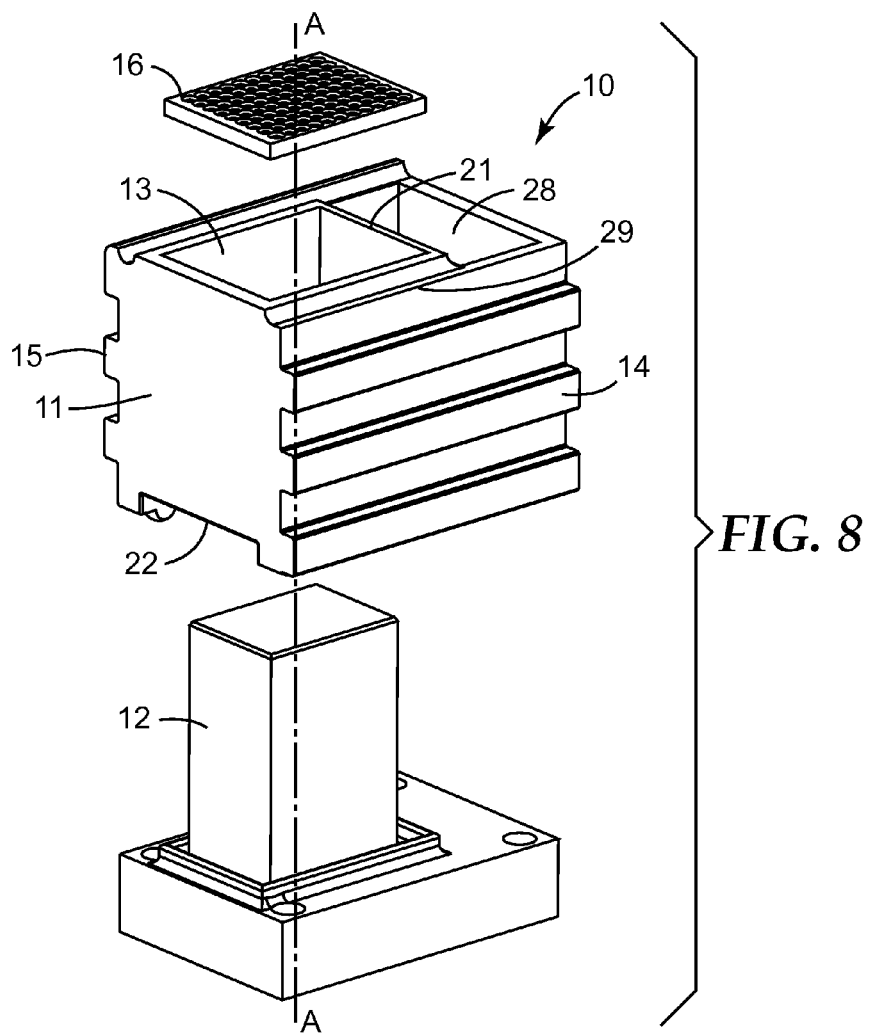
FIG. 8 is a perspective view of the material cartridge according to an embodiment of the invention.

FIG. 8 shows the material cartridge 10 according to the invention in more detail. The cartridge 10 comprises a body 11 which has a channel 13 through the body 11. In the example the channel has a generally rectangular cross-section over at least part of the overall length of the channel. The skilled person will however recognize that other shapes are possible without departing from the invention. The channel 13 in the example extends along a longitudinal axis A. The cartridge 10 is shown in an appropriate orientation for use, in which the longitudinal axis A is oriented substantially vertical. The channel further forms an upper cartridge opening 21 and a lower cartridge opening 22 (not visible in this view) in the body 11. Further the cartridge comprises a support 16. The support 16 is adapted for movable arrangement within the channel 13. In particular the support 16 has an overall cross-section which approximately corresponds in shape and size to the channel cross-section. Thus with the support 16 appropriately placed in the channel 13 a reservoir may be formed in the body between the upper cartridge opening 21, the support 16 and the channel walls. The reservoir thus has a movable reservoir bottom formed by the support 16, and reservoir side walls formed by walls of the channel 13. The reservoir preferably allows for holding a build-up material, for example a powder material, or for accommodating an object built up from build-up material. The cartridge due to the movable support 16 further preferably allows for moving and positioning the build-up material within the channel 13.

In the example the cartridge comprises a plunger 12 which is also adapted for movable arrangement within the channel 13. The plunger 12 may be used for moving and positioning the support 16 within the channel 13 in a dimension parallel to the longitudinal axis A. Therefore the plunger 12 may be inserted in the channel 13 from the lower cartridge opening 22 toward the upper cartridge opening 21. The skilled person will recognize that the support and the plunger in other examples may form one piece, for example may form one monolithic piece.

The cartridge 10 further has a first structured side face 14 and a second structured side face 15. The first and second side faces 14, 15 face away from each other. The structure of the first structured side is complementary in shape to the structure of the second structured side such that two cartridges of the same configuration can be arranged side by side with their complementary side faces meshing with one another. Therefore two cartridges may be placed with their side faces adjacent each other and may in this position retain each other in a dimension generally parallel to the longitudinal axis A.

The body 11 has a spillover cavity 28. The spill over cavity 28 is adapted to receive excess material, for example excess powder material. Further the body 11 has one or more spillover grooves 29 preferably arranged adjacent or at least partially surrounding the cartridge opening 21. The spillover grooves 29 may provide for material spilled outside the cartridge opening 21 to be guided toward the spillover cavity where the material may be gathered. Material may thus be prevented from flowing into a chamber of a rapid prototyping device, and accordingly the rapid prototyping device may be kept generally free from material. Therefore efforts for cleaning the rapid prototyping device may be minimized, which in particular may otherwise be required between building up different objects types from of different types of materials in sequence.

Figure 9:
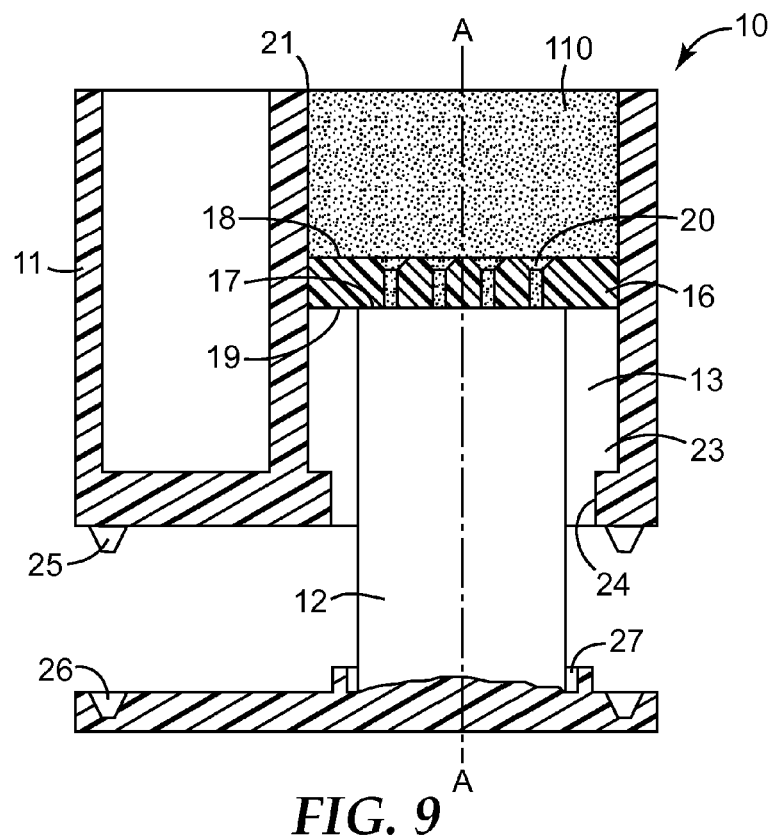
FIG. 9 is a cross-sectional view of the material cartridge of FIG. 8 at one stage in use.

FIG. 9 shows a cross-sectional view of the cartridge 10 in which the reservoir is filled with a build-up material 110. The build-up material in the example is a powder material which in the situation shown is present in the form of a bulk of loose grains. The support 16 is placed within the channel 13 and carries the build-up material 110. The plunger 12 is placed in the channel and carries the support 16. In an embodiment (not shown) the plunger and the support may be retained at one another by a magnetic connection. For example one of the plunger or the support may comprise a magnet and the other one of the plunger and the support may comprise a further magnet or a magnetic metal. Therefore moving the plunger 12 in a direction parallel to the longitudinal axis A preferably causes the support 16 and consequently also the powder 110 to move in the same direction. Thus the plunger 12 may be used to move and position the build-up material relative to the cartridge opening 21 in the cartridge 10.

The plunger 12 may be dimensioned to form a loose fit with the walls forming the channel 13 as illustrated. Accordingly a circumferential gap 23 may exist between the plunger 12 and the walls forming the channel 13. The gap is preferably sufficient to allow a powder material to pass through. Therefore the plunger 12 may be prevented from getting stuck within the channel 13 from powder material jamming between the plunger 12 and the channel walls. In contrast the support 16 is preferably sized and shaped such that build-up material present in the channel 13 is generally prevented from escaping through a gap between the support 16 and the channel walls. In an embodiment (not shown) the support may have a seal (for example one made of an elastomeric material or a non-woven material) for sealing a gap between the support and the channel walls. The cartridge 10 and the plunger 12 are adapted to align relative to each other in a dimension or a plane laterally to the longitudinal axis A. In the example the body 11 has at least one alignment cone 25 and the plunger has at least one corresponding alignment cavity 26. The skilled person will appreciate that alternatively the body 11 may have an alignment cavity and the plunger may have a corresponding alignment cone. The alignment cone 25 and the alignment cavity 26 preferably mate with one another at a certain position of the plunger 12 and the body 11 relative to one another along a dimension parallel to the longitudinal axis A. The alignment cone 25 and the alignment cavity 26 during mating due to their conical shape preferably urge the plunger 12 and the body 11 toward a predefined lateral position of the longitudinal axis relative to each other. In the example the lateral alignment of the plunger 12 and the body 11 is preferably only provided in an end position of the plunger 12 and the body 11 relative to one another along a dimension parallel to the longitudinal axis A, in particular in a situation in which the plunger 12 is placed in the body 11 as far as possible. In use of the cartridge 10 with a rapid prototyping device this may allow the plunger 12 and the body 11 to be appropriately positioned initially, for example during insertion of the cartridge 10 in a chamber of the device. Further due to the rapid prototyping device providing for the plunger 12 to be moved only substantially along the longitudinal axis the lateral position of the plunger 12 and the body 11 relative to each other is preferably substantially maintained in positions outside the end position, even though the plunger 12 and the body 11 may not be in touch in those outside positions. This preferably provides for friction and blocking of the piston 12 in the body 11 to be generally avoided during use of the cartridge 10. Accordingly the accuracy of the positioning of the support may be maximized because a stick-slip effect of the plunger 12 within the body 11 may be minimized. The skilled person will recognize other configurations allowing for aligning the plunger 12 relative to the body 11, however the illustrated configuration was found to operate well.

The support 16 may further itself be permeable for the build-up material. In the example the support 16 has a plurality of through-holes 20 which extend between an upper support face 18 and a lower support face 19 of the support 16. The upper support face 18 is adapted to carry the powder material and the lower support face 19 is adapted to cooperate with the piston 12. In the situation shown the plunger 12 blocks with an upper plunger face 17 the though-holes 20. Therefore in this situation the build-up material 110 is preferably prevented from escaping from the reservoir although the support itself is permeable. The cartridge 10 in the situation shown in FIG. 9 may for example be used to provide a build-up material in a rapid prototyping device in which this build-up material may be used to build up an object. The cartridge of the invention therefore may allow for quickly and conveniently providing a build-up material in a rapid prototyping device.

The plunger 12 may further have a material trap 27 arranged around the plunger in a plane laterally to the longitudinal axis A. The material trap 27 preferably avoids small amounts of build-up material from escaping entirely from the cartridge 10. Therefore the cartridge of the invention may be removable from a rapid prototyping device without leaving behind substantial amounts of build-up material. This further may enable or at least facilitate the use of different build-up materials sequentially in a single rapid prototyping device.

Figure 10:
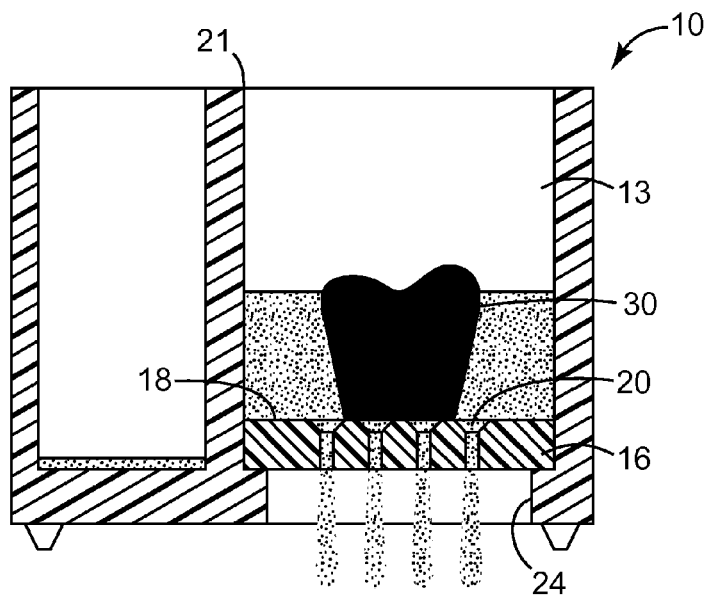
FIG. 10 is a cross-sectional view of the material cartridge of FIG. 8 at a further stage in use.

FIG. 10 relative to FIG. 9 illustrates the cartridge 10 in an alternative use for receiving an object during a built up process in a rapid prototyping device. In particular the cartridge 10 may be placed in the rapid prototyping device in an empty stage (without a build-up material present in the channel). In an initial situation the support 16 may be positioned with its upper face 18 flush with the cartridge opening 21. During the build up process the support may be lowered in incremental steps for receiving several layers of powder material. Thus an object 30 may be built up on the support 16 by the rapid prototyping device in the same manner as it is described in FIGS. 2 to 6 but just within the cartridge and not directly in a chamber of the rapid prototyping device.

The illustrated situation in FIG. 10 shows the cartridge 10 with the finished object (in this case a dental restoration precursor). Relative to FIG. 9 the piston is removed from the cartridge in the situation illustrated in FIG. 10. The cartridge 10 has a detent 24 on which the support 16 rests. The detent 24 therefore prevents the support 16 from falling off from the channel 13 in a situation where a plunger is not present. Further the through-holes 20 are unblocked so that the excessive build-up material in which the object may be embedded can be released through the support. The through-holes 20 are preferably dimensioned such that loose build-up material can pass through. Further the through-holes 20 are preferably dimensioned such that the object cannot pass through the through-holes but is retained by the support 16. Thus the support may be used as a screen for separating the object 30 from loose build-up material.

For removing the build-up material from the cartridge through the through-holes the cartridge may be shaken or vibrated, in particular in case a powder material is used. Therefore residual loose build-up material at the object may be minimized. The cartridge may be placed on a shaker unit for shaking, for example one as it is typically present in a dental technician laboratory for densifying plaster. Therefore the cartridge of the invention preferably allows for minimizing costs and efforts for removing of a built up object from surrounding loose build-up material.

Figure 11:
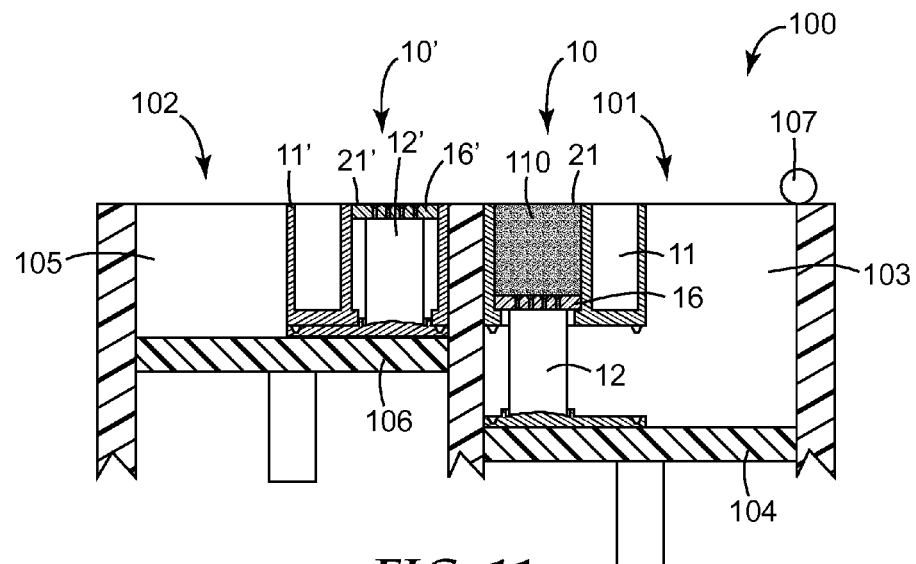
FIGS. 11-13 are cross-sectional views of the rapid prototyping device of FIG. 1 illustrating a process of building up an object according to embodiments of the invention.
Figure 12:
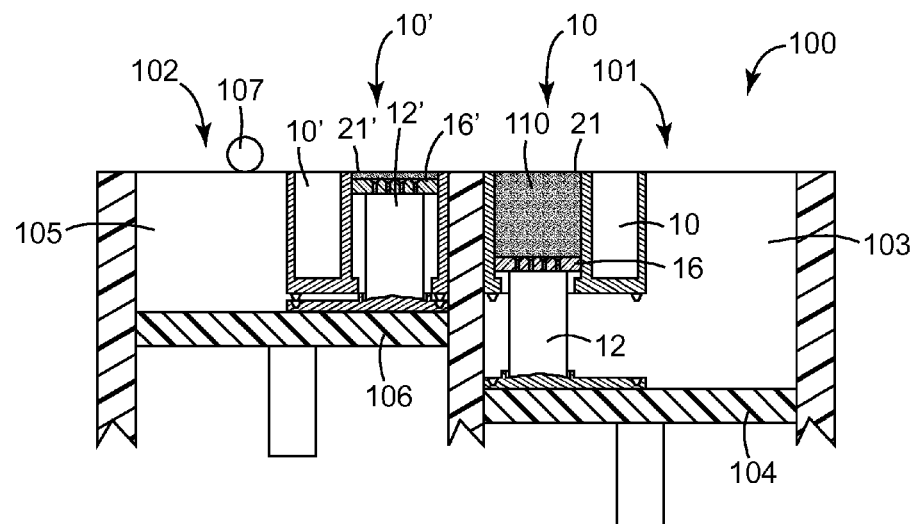
Figure 13:
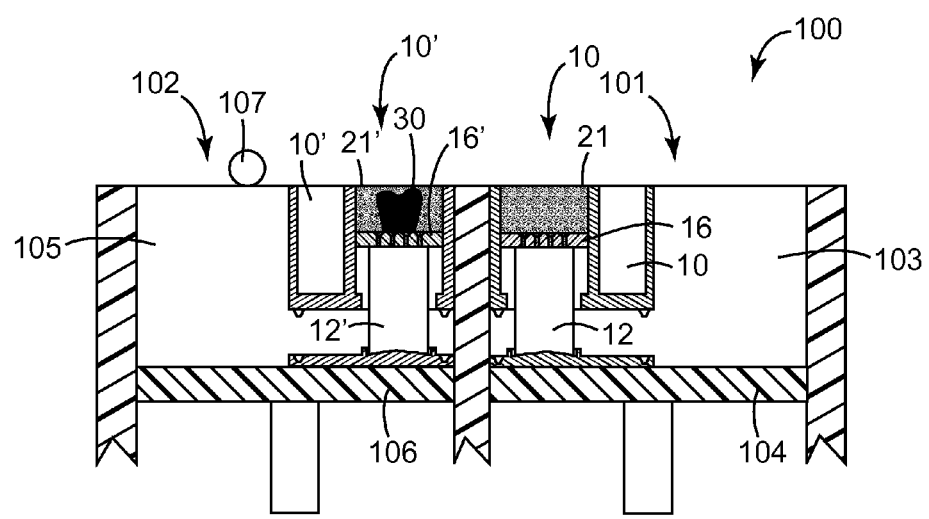

FIG. 11 to FIG. 13 illustrate a process of building up an object in the rapid prototyping device 100 by use of two identical cartridges 10, 10'. The overall process is generally the same as illustrated in FIGS. 1 to 7 and therefore not described in some details already mentioned above.

FIG. 11 shows the cartridge 10 filled with a powder material 110. The support 16 is positioned below the cartridge opening 21 so that a reservoir for the powder material 110 is formed. Accordingly the plunger 12 is positioned somewhat retracted from an end position within the body 11. The body 11 of the cartridge 10 is fixed at the second side walls 103 of the second chamber 101 of the rapid prototyping device 100.

The plunger 12 rests on the movable second base 104 of the rapid prototyping device 100. Thus as the second base 104 moves up or down the plunger 12 follows that movement and causes the support 16 to move.

Another cartridge 10' which is generally identical to the cartridge 10 is prepared for receiving an object in the first chamber 102. Therefore the support 16' is positioned flush with the cartridge opening 21'. Further the plunger 12' is positioned at an end position within the body 11'. The body 11' of the cartridge 10 is fixed at the first side walls 105 of the second material chamber 102 of the rapid prototyping device 100. The plunger 12' rests on the first base 106 of the rapid prototyping device 100 and thereby can be moved and positioned.

FIG. 12 shows the rapid prototyping device 100 and the cartridges 10, 10' with a portion of the powder material transferred from the cartridge 10 to the cartridge 10'. The plunger 12 and accordingly the support 16 are lifted relative to the position shown in FIG. 11. The powder portion displaced above the cartridge opening 21 is transferred into the cartridge 10'. Further the plunger 12' and accordingly the support 16' are lowered relative to the position shown in FIG. 11. The resulting space between the cartridge opening 21' and the support 16' is filled with a layer of powder material.

FIG. 13 relative to FIG. 12 shows the rapid prototyping device 100 and the cartridges 10, 10' with a larger portion of the powder material transferred from the cartridge 10 to the cartridge 10' and with an object built up in the reservoir of the cartridge 10'. The object is formed from solidified powder material, for example from adjoined or fused powder grains and/or from powder grains held in place by a hardened binder. The cartridges 10, 10' may be removed from the rapid prototyping device and new cartridges may be provided into the device. Therefore the cartridge of the invention allows for the rapid prototyping device to be prepared for a new build-up job at a minimized time after finishing a previous job.

Figure 14:
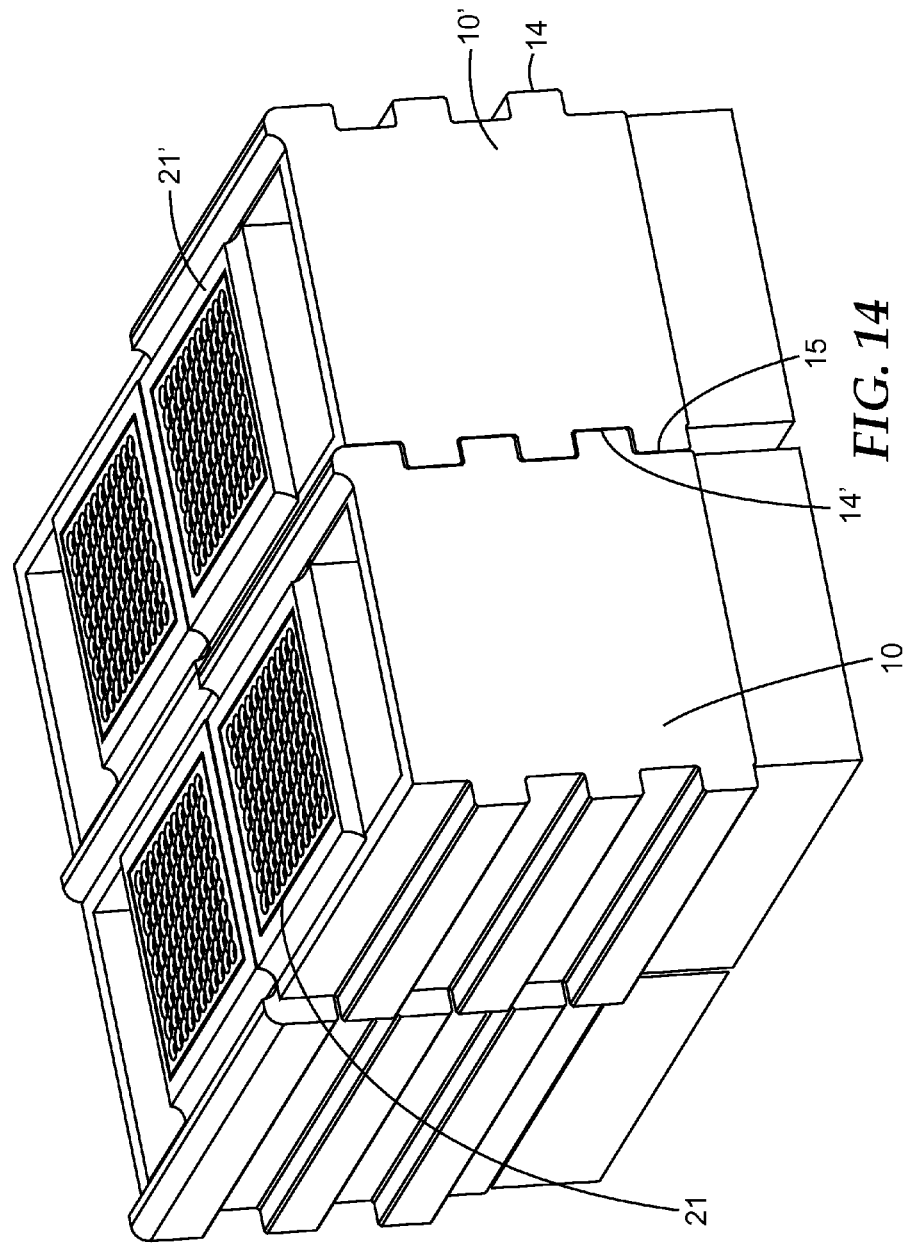
FIG. 14 is a perspective view of the device shown in FIG. 1 with two material cartridges and cooperating two cartridges for building up objects according to an embodiment of the invention.

FIG. 14 shows two cartridges arranged in one chamber of the rapid prototyping device and further two cartridges in another chamber of the device. Thus two different objects may be built up in parallel or simultaneously. Further the cartridges that are arranged laterally to a direction of the recoater motion for transferring material may contain different build-up materials, for example differently colored materials. Therefore the cartridge of the invention may also allow for maximizing the throughput of the rapid prototyping device. Further a rapid prototyping device configured for processing only one material at a time may be used for processing a plurality of materials generally simultaneously by help of the present invention.

In this example the use of the structured sides of the cartridge is illustrated. The cartridge 10 arranged next to the cartridge 10' has the structured side 15. The structured side 15 of the cartridge 10 is mated with a complementary shaped structured side 14' of the cartridge 10'. The structured side 14' corresponds in shape to the first structured side 14 of the cartridge 10. The first and second structured sides are adapted in shape such that two similar cartridges fitted with one another at their sides can be brought in a predefined position relative to each other in at least one dimension. In the example the cartridges 10 and 10' by use of the structured sides are positioned such that the openings 21, 21' are substantially flush with one another.

Figure 15:
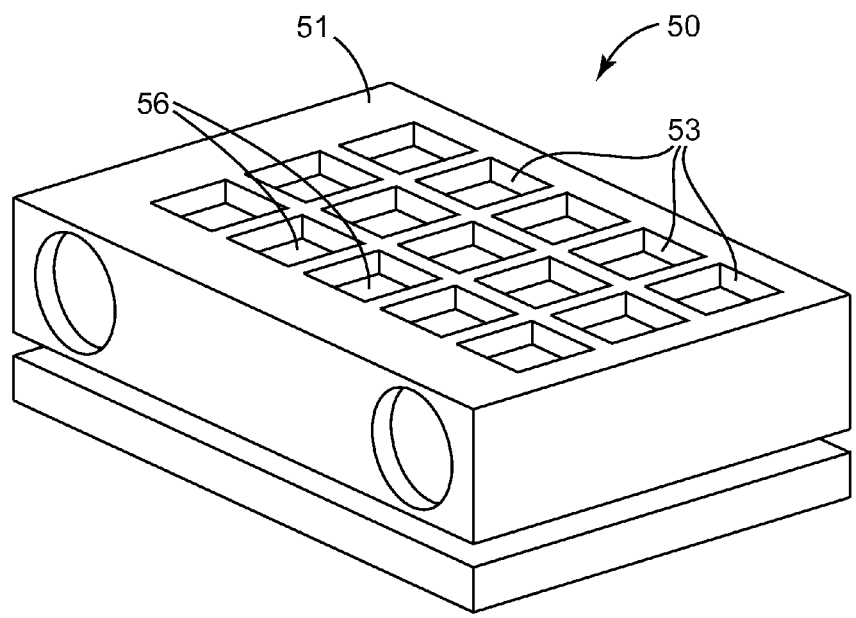
FIG. 15 is a perspective view of the material cartridge according to a further embodiment of the invention.

FIG. 15 shows a cartridge 50 which has a body 51 forming a plurality of channels 53. A plurality of supports 56 may be movably arranged within the channels 53. The skilled person will recognize that one support or plunger can be used as an alternative of using several supports and/or plungers. In this case the support or plunger may have a plurality of protrusions which are adapted to be arranged movably within the channels 53. The cartridge may otherwise be similar or identical to the cartridge shown in FIGS. 8 to 10. Such an embodiment may allow building up a set of objects in one cartridge, and the cartridge may allow this set to be kept together. For example a build-up job for one certain customer may include a set of several objects to be built up. In this case a job of one customer may be kept in one or more cartridges. Further different cartridges may be used for processing different materials. Therefore such a configuration may generally help minimizing logistic efforts in mass manufacturing of dental restorations.

The invention claimed is:

1. A system comprising a rapid prototyping device for building up a three-dimensional object from a build-up material, and a material cartridge;
   the rapid prototyping device comprising:
      at least a first chamber for building up the object from the build-up material; and
   the cartridge comprising:
      a body into which a channel extends;
      the channel forming a first cartridge opening in the body;
      a support being adapted to be movably arranged within the channel for a movement relative to the first cartridge opening;
      the cartridge being adapted to be removably placed in the first chamber; and
      the cartridge being adapted to form a reservoir;
   wherein the rapid prototyping device and the cartridge are adapted such that the rapid prototyping device can move the support of the cartridge, and wherein the rapid prototyping machine is adapted such that the presence of a cartridge is optional for building up the object so that the object can be built up in the reservoir of a cartridge present in the first chamber and in the first chamber outside the reservoir in absence of the cartridge.

2. The system of claim 1, in which the rapid prototyping device further comprises a second chamber for providing at least a component of the build-up material, and wherein the cartridge is further adapted to be removably placed in the second chamber, and wherein the rapid prototyping machine is adapted such that the presence of a cartridge is optional for providing the build-up material so that the build-up material can be provided in the reservoir of a cartridge present in the first chamber and in the second chamber outside the reservoir in absence of the cartridge.

3. The system of claim 1, further comprising a plunger which is adapted to cooperate with the cartridge for moving the support.

4. The system of claim 3, wherein the channel extends with a generally uniform cross-section within the body along a longitudinal axis of the cartridge.

5. The system of claim 3, wherein the channel extends between the first cartridge opening and an opposite second cartridge opening in the body, and further being adapted such that the plunger can be at least partially arranged within the channel between the support and the second cartridge opening.

6. The system of claim 3, being adapted such that the plunger can position the support between a first position in which the support is spaced relative to the first cartridge opening and a second position in which the support is substantially flush with the first cartridge opening.

7. The system of claim 6, in which the plunger and the body are adapted to self-align relative to one another in the second position.

8. The system of claim 3, wherein the support comprises a plurality of through-holes, the system being further adapted such that the plunger blocks the through-holes during cooperation with the support for moving the support, and wherein the piston opens the through-holes in a situation where the plunger is removed from the support.

9. The system of claim 1, wherein the body comprises a spillover cavity adjacent the first cartridge opening.

10. The system of claim 1, wherein the cartridge has a first side face having a first structure and a second side face having a second structure, the first and second faces facing away from each other, and wherein the first and second structures have complementary shapes.

11. The system of claim 1, wherein at least a component of the build-up material is a powder, and wherein the channel is adapted to hold the powder.

* * * * *